US011877855B2

(12) United States Patent
Jeong et al.

(10) Patent No.: US 11,877,855 B2
(45) Date of Patent: Jan. 23, 2024

(54) APPARATUS FOR MEASURING ELECTROCARDIOGRAM AND METHOD OF RECORDING ECG SIGNALS MERGED WITH USER INPUT

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Bang Won Lee, Gyeonggi-do (KR)

(73) Assignee: ATSENS CO., LTD., Gyeonggi-do (KR)

( * ) Notice: Subject to any disclaimer, the term of this patent is extended or adjusted under 35 U.S.C. 154(b) by 307 days.

(21) Appl. No.: 16/998,440

(22) Filed: Aug. 20, 2020

(65) Prior Publication Data

US 2022/0054034 A1 Feb. 24, 2022

(51) Int. Cl.
*A61B 5/333* (2021.01)
*A61B 5/00* (2006.01)
(Continued)

(52) U.S. Cl.
CPC ............ *A61B 5/333* (2021.01); *A61B 5/0006* (2013.01); *A61B 5/7225* (2013.01); *A61B 5/749* (2013.01);
(Continued)

(58) Field of Classification Search
CPC ..... A61B 5/333; A61B 5/0006; A61B 5/7225; A61B 5/749; A61B 5/02055; A61B 5/28;
(Continued)

(56) References Cited

U.S. PATENT DOCUMENTS

| 7,547,280 B2 | 6/2009 | Yanagihara et al. |
| 2014/0148719 A1 | 5/2014 | Yang et al. |

(Continued)

FOREIGN PATENT DOCUMENTS

| CN | 204698548 U | * 10/2015 | ........... A61B 5/0006 |
| CN | 107871535 | 4/2018 | |

(Continued)

OTHER PUBLICATIONS

Office Action issued in corresponding Korean application No. 1020190041055, dated Sep. 9, 2020.
(Continued)

*Primary Examiner* — Michael W Kahelin
(74) *Attorney, Agent, or Firm* — Guntin & Gust, PLC; Miyoung Shin

(57) ABSTRACT

An apparatus for measuring an electrocardiogram and storing an electrocardiogram signal merged with a user input includes: a signal detector outputting an electrocardiogram analog signal by detecting an electrical signal from the heart of an object; a signal converter receiving the electrocardiogram analog signal and converting the electrocardiogram analog signal into an electrocardiogram digital signal; an input unit receiving at least one type of user input from among a voice input, a button input, a touch input, and a motion input; a processor receiving the user input, merging the electrocardiogram digital signal with the user input, and storing the electrocardiogram digital signal in an internal memory; and a communicator communicating with an external terminal to transmit the electrocardiogram digital signal to the external terminal.

16 Claims, 12 Drawing Sheets

(51) Int. Cl.
*A61B 5/259* (2021.01)
*G06F 3/02* (2006.01)
*H04L 67/12* (2022.01)

(52) U.S. Cl.
CPC ............... *G06F 3/02* (2013.01); *A61B 5/259* (2021.01); *H04L 67/12* (2013.01)

(58) Field of Classification Search
CPC .. A61B 5/24; A61B 5/259; A61B 5/00; G06F 3/02; H04L 67/12; H04W 4/80; A61N 1/00
See application file for complete search history.

(56) References Cited

U.S. PATENT DOCUMENTS

| | | |
|---|---|---|
| 2017/0000370 A1 | 1/2017 | Hyde et al. |
| 2017/0155427 A1 | 6/2017 | Hasan et al. |
| 2018/0085021 A1* | 3/2018 | Chakravarthy ...... A61B 5/0006 |
| 2018/0206751 A1 | 7/2018 | Patil et al. |
| 2018/0279879 A1* | 10/2018 | Both ........................ A61B 5/25 |
| 2018/0302189 A1 | 10/2018 | Harrod, IV et al. |
| 2019/0336032 A1* | 11/2019 | Gill ...................... A61B 5/0031 |
| 2021/0085201 A1 | 3/2021 | Saitoh et al. |

FOREIGN PATENT DOCUMENTS

| | | | |
|---|---|---|---|
| EP | 1946698 | 7/2008 | |
| JP | 2005152401 A | 6/2005 | |
| JP | 2017143951 A | 8/2017 | |
| JP | 2019130287 A | 8/2019 | |
| KR | 10-2008-0036755 | 4/2008 | |
| KR | 10-1381136 | 4/2014 | |
| WO | 2009112976 | 9/2009 | |
| WO | WO-2009112976 A1 * | 9/2009 | ........... A61B 5/0006 |
| WO | WO-2019073288 A1 * | 4/2019 | |

OTHER PUBLICATIONS

Office Action issued in corresponding JP Application No. 2020-143553, dated Nov. 2, 2021, 2 pages.
Extended European Search Report for EP Application 20193176.3, dated May 11, 2021.
Partial European Search Report for EP Application 20193176, completed Feb. 10, 2021.

* cited by examiner

APPARATUS FOR MEASURING ELECTROCARDIOGRAM AND METHOD OF RECORDING ECG SIGNALS MERGED WITH USER INPUT

FIELD

One or more embodiments relate to an apparatus for measuring an electrocardiogram and a method of recording electrocardiogram signals merged with a user input.

BACKGROUND

In order to maintain human life, there is a need for a process of enabling blood released by the heartbeat to flow along the arteries to all parts of the body without clogging and returning blood through the veins back to the heart. Accordingly, oxygen and nutrients may be supplied to the body's tissues, and consumed wastes may be removed through the metabolism.

However, when the human heart is in a poor condition, blood may not be properly delivered to particular parts of the body or a blood clot or embolism may occur in the blood. As a result, blood may become cloudy, and the cloudy blood may block capillaries, in particular tissues of the body, and cause tissue necrosis, and thus, the human life may be in danger. Therefore, in addition to clinical examinations, imaging tests and the like have been used to examine whether or not the heart is abnormal. Also, as an early diagnosis method, a method of determining whether or not a patient has an abnormality in the heart by measuring an electrocardiogram and displaying the measured electrocardiogram signal in a graph format has also been widely used.

In other words, an electrocardiogram refers to recording of a potential change in the surface of the body causing the mechanical activity of the heartbeat, such as contraction or expansion of the heart muscle. The electrocardiogram is a non-vascular test that is simply measured, is easily reproduced, is easily repetitively recorded, and is inexpensive to test. The electrocardiogram has been used helpfully to diagnose arrhythmia and coronary artery disease (cardiac artery disease) and to monitor the progress of cardiac patients.

In general, the sensing electrodes of the electrocardiogram are attached to the upper left and right and lower left and right of the chest. And potential differences are detected according to the location of the sensor.

SUMMARY

One or more embodiments include an apparatus for measuring an electrocardiogram and recording an electrocardiogram digital signal in association with a user input.

The technical problems to be solved by the present embodiment are not limited to the technical problems as described above, and other technical problems may be inferred from the following embodiments.

Additional aspects will be set forth in part in the description which follows and, in part, will be apparent from the description, or may be learned by practice of the presented embodiments of the disclosure.

According to one or more embodiments, an apparatus for measuring an electrocardiogram includes: a signal detector outputting an electrocardiogram analog signal by detecting an electrical signal from the heart of an object; a signal converter receiving the electrocardiogram analog signal and converting the electrocardiogram analog signal into an electrocardiogram digital signal; a processor storing the electrocardiogram digital signal in a memory, transmitting the electrocardiogram digital signal to a user terminal through a near field communication network, and controlling the electrocardiogram digital signal to be stored in a memory of the user terminal; and a power supply unit supplying power to the signal detector, the signal converter, the memory, and the processor, wherein the electrocardiogram digital signal is associated with a user input generated from the user terminal to generate electrocardiogram measurement data.

According to one or more embodiments, an apparatus for measuring an electrocardiogram and associating an electrocardiogram signal with a user input to generate electrocardiogram measurement data, includes: a signal detector outputting an electrocardiogram analog signal by detecting an electrical signal from the heart of an object; a signal converter receiving the electrocardiogram analog signal and converting the electrocardiogram analog signal into an electrocardiogram digital signal; a processor receiving a user input from a user terminal, storing, in a memory, the electrocardiogram digital signal in association with the user input, transmitting the electrocardiogram digital signal to the user terminal through a near field communication network, and controlling the electrocardiogram digital signal to be stored in a memory of the user terminal; and a power supply unit supplying power to the signal detector, the signal converter, the memory, and the processor.

The processor may transmit an input user input posting signal to the user terminal and receive, from the user terminal, a user input that is input in response to the user input posting signal.

The electrocardiogram digital signal may be synchronized with the user input by using generation time information in the user terminal in which the user input is generated.

The processor may additionally generate at least one tag of a tag corresponding to an apparatus temperature value sensed through a provided sensor unit, a tag corresponding to the momentum acquired through the provided sensor unit, and a tag corresponding to a heart rate calculated by analyzing the electrocardiogram digital signal, further insert the at least one tag into the electrocardiogram digital signal, and store the electrocardiogram digital signal in the memory.

The processor may divide the electrocardiogram digital signal into preset time intervals and transmit, to the user terminal, a part of a k-$1^{st}$ electrocardiogram digital signal for a $k^{th}$ time interval.

When the user input is a touch input, the electrocardiogram digital signal may be stored in the memory or a memory of the user terminal by generating a tag corresponding to touch sensitivity of the user input and inserting the tag into the electrocardiogram digital signal on the basis of generation time information of the touch input.

According to one or more embodiments, an apparatus for measuring an electrocardiogram includes: a signal detector outputting an electrocardiogram analog signal by detecting an electrical signal from the heart of an object; a signal converter receiving the electrocardiogram analog signal and converting the electrocardiogram analog signal into an electrocardiogram digital signal; an input unit receiving at least one type of user input from among a voice input and a text input; a processor storing, in a memory, the electrocardiogram digital signal in association with the user input by using generation time information of the user input; and a power supply unit supplying power to the signal detector, the signal converter, the memory, and the processor.

The processor may transmit the electrocardiogram digital signal to a user terminal through a near field communication network and control the electrocardiogram digital signal to be stored in a memory of the user terminal.

The processor may determine an insertion location of the user input in the electrocardiogram digital signal by using generation time information of the user input and store, in the memory, the electrocardiogram digital signal synchronized with the user input at the insertion location.

The processor may additionally generate at least one of a tag corresponding to an apparatus temperature value detected through a provided sensor unit, a tag corresponding to the momentum acquired through the provided sensor unit, and a tag corresponding to a heart rate calculated by analyzing the electrocardiogram digital signal, insert the at least one tag into the electrocardiogram digital signal, and store the electrocardiogram digital signal in the memory.

The apparatus for measuring an electrocardiogram may divide the electrocardiogram digital signal into preset time intervals and transmit, to the user terminal, a part of a k-$1^{st}$ electrocardiogram digital signal for a $k^{th}$ time interval.

When the user input is a touch input, the processor may generate a tag corresponding to touch sensitivity of the user input, insert the tag into the electrocardiogram digital signal on the basis of generation time information of the touch input, and store the electrocardiogram digital signal in the memory.

The processor may further insert, into the electrocardiogram digital signal, a message received from the user terminal.

According to one or more embodiments, a method of measuring an electrocardiogram, includes: outputting an electrocardiogram analog signal by detecting an electrical signal from the heart of an object, the outputting being performed by an apparatus for measuring an electrocardiogram; receiving the electrocardiogram analog signal and converting the electrocardiogram analog signal into an electrocardiogram digital signal, the receiving and converting being performed by the apparatus; and storing the electrocardiogram digital signal in a memory and transmitting the electrocardiogram digital signal to a user terminal through a near field communication network, the storing and transmitting being performed by the apparatus, wherein the electrocardiogram digital signal is modified in the user terminal in association with a user input generated by the user terminal.

According to one or more embodiments, a method of measuring an electrocardiogram, includes: outputting an electrocardiogram analog signal by detecting an electrical signal from the heart of an object, the outputting being performed by an apparatus for measuring an electrocardiogram; receiving the electrocardiogram analog signal and converting the electrocardiogram analog signal into an electrocardiogram digital signal, the receiving and converting being performed by the apparatus; receiving, by the apparatus, a user input from a user terminal; storing, in a memory, the electrocardiogram digital signal in association with the user input by using generation time information of the user input and transmitting the electrocardiogram digital signal to the user terminal through a near field communication network, the storing and transmitting being performed by the apparatus.

The electrocardiogram digital signal may be synchronized with the user input by using generation time information in the user terminal in which the user input is generated.

Before the storing, the method may further include: additionally generating at least one of a tag corresponding to an apparatus temperature value detected through a provided sensor unit, a tag corresponding to the momentum acquired through the provided sensor unit, and a tag corresponding to a heart rate calculated by analyzing the electrocardiogram digital signal and storing, in the memory, the electrocardiogram digital signal in association with the at least one tag.

The transmitting may include: dividing the electrocardiogram digital signal into preset time intervals and transmitting, to the user terminal, a part of a k-$1^{st}$ electrocardiogram digital signal for a $k^{th}$ time interval.

When the user input is a touch input, the electrocardiogram digital signal may be stored in the memory by generating a tag corresponding to touch sensitivity of the user input and inserting the tag into the electrocardiogram digital signal on the basis of generation time information of the touch input According to one or more embodiments, a method of measuring an electrocardiogram includes: outputting an electrocardiogram analog signal by detecting an electrical signal from the heart of an object, the outputting being performed by an apparatus for measuring an electrocardiogram; receiving the electrocardiogram analog signal and converting the electrocardiogram analog signal into an electrocardiogram digital signal, the receiving and converting being performed by the apparatus; receiving, by the apparatus, at least one type of user input from among a voice input and a text input; storing, in a memory, the electrocardiogram digital signal in association with the user input by using generating time information of the user input, the storing being performed by the apparatus; and by transmitting the electrocardiogram digital signal to a user terminal through a near field communication network, the transmitting being performed the apparatus.

The method may further include storing the electrocardiogram digital signal in a memory of the user terminal.

The storing may include: determining an insertion location of the user input in the electrocardiogram digital signal by using generation time information of the user input and storing, in the memory, the electrocardiogram digital signal synchronized with the user input at the insertion location.

Before the storing, the method may further include: additionally generating at least one of a tag corresponding to an apparatus temperature value detected through a provided sensor unit, a tag corresponding to the momentum acquired through the provided sensor unit, and a tag corresponding to a heart rate calculated by analyzing the electrocardiogram digital signal and storing, in the memory, the electrocardiogram digital signal in association with the at least one tag.

The transmitting may include: dividing the electrocardiogram digital signal into preset time intervals and transmitting, to the user terminal, a part of a k-$1^{st}$ electrocardiogram digital signal for a $k^{th}$ time interval.

The storing may include: when the user input is a touch input, generating a tag corresponding to touch sensitivity of the user input, inserting the tag into the electrocardiogram digital signal on the basis of generation time information of the user input, and store the electrocardiogram digital signal in the memory.

The method may further include: further inserting, into the electrocardiogram digital signal, a message received from the user terminal.

A computer program according to one or more embodiments may be stored on a medium to execute, by using a computer, any one of methods according to one or more methods.

In addition, provided are other methods, other systems, and computer-readable recording media recording thereon a computer program for executing the method.

Other aspects, features, and advantages than those described above will become apparent from the following drawings, claims, and detailed description.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
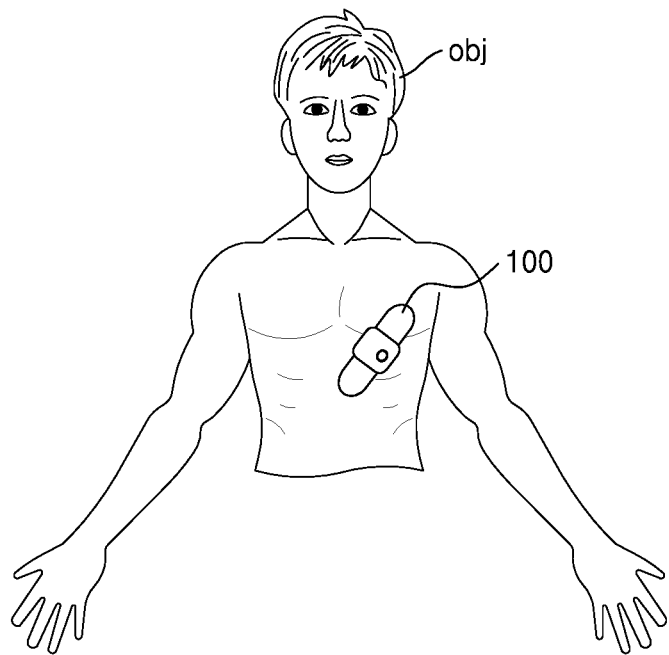
FIG. 1A is a view of an embodiment of an apparatus for measuring an electrocardiogram, according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

With respect to the terms in the various embodiments, the general terms which are currently and widely used are selected in consideration of functions of structural elements in the various embodiments of the present disclosure. However, meanings of the terms can be changed according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er," "-or," and "module" described in the specification mean units for processing at least one function and operation and can be implemented by hardware components or software components and combinations thereof.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, one or more embodiments will be described in detail with reference to the accompanying drawings.

Atrial fibrillation is one of the most common kinds of arrhythmia clinically, and an overall prevalence thereof is about 0.4% to 0.9%. From the age of 40 onwards, the prevalence of atrial fibrillation increases by about 0.1% to about 0.2% each year and increases to about 2% to about 4% when the age is 60 years or older. When atrial fibrillation is accompanied, atrial-to-ventricular synchronization is lost and ventricular diastolic is shortened, thereby causing respiratory difficulty and cardiac failure. Also, in patients with atrial fibrillation, a thrombus is created in the atrium and causes a systemic embolism such as cerebral infarction, thereby increasing a mortality rate. The increase in the occurrence of atrial fibrillation along with the increase in the aged population has significant health and sociological meanings in this regard. Because paroxysmal atrial fibrillation may develop into chronic atrial fibrillation, the prediction and diagnosis of the occurrence risk of paroxysmal atrial fibrillation are significant.

Among ECG signal components, a P-wave component has been used as significant information for predicting and diagnosing such atrial fibrillation. Therefore, it is highly significant to develop electrocardiogram measuring apparatuses capable of generating ECG signals in which P-wave components are well expressed.

In particular, recently, large hospitals have used expensive ultrasonic medical devices to accurately observe the heart conditions, and thus, the utilization of electrocardiogram measuring apparatuses has gradually decreased. However, P-wave components may not be measured even through ultrasonic medical devices provided in large hospitals or the like.

According to one or more embodiments, a P-wave component from among ECG signal components may be further enhanced in a process of generating an input analog ECG signal. A P-wave component may be enhanced by applying different conversion gains to a signal in a PR interval and a signal in the remaining interval.

According to one or more embodiments, signal gain may be an element for adjusting the magnitude of an electrocardiogram signal in a process of converting an electrocardiogram analog signal into an electrocardiogram digital signal. For example, the gain of a PR interval may be 0×66, and the gain of the remaining interval may be 0×33. Note that 0×66 and 0×33 are hexadecimal numbers that determines signal gain. As the gain of the PR interval is greater than that of the remaining interval, the magnitude of a P-wave component may be increased.

In one or more embodiments, when the gain is set to be constantly high in the entire interval of an electrocardiogram (ECG) signal, signal stability caused by various types of noise, such as body noise and noise due to motions, may be lowered.

FIG. 1A is a view of a network environment of an apparatus 100 for measuring an electrocardiogram, according to one or more embodiments.

As illustrated in FIG. 1A, the apparatus 100 for measuring an electrocardiogram (hereinafter referred to as the electrocardiogram measuring apparatus 100) is an apparatus which is mounted on an object obj noninvasively or invasively to detect an electrocardiogram according to the heartbeat of the object obj. Here, the object obj may be a human, an animal, or part of the body of a human or animal such as the chest but is not limited thereto. The object obj may include all types of objects from which electrocardiograms may be detected or measured. Also, an electrocardiogram is a graph that records changes in a potential appearing on the surface of the body according to the mechanical activity of the heartbeat such as contraction/expansion of the myocardium. Here, the meaning "detect an electrocardiogram" may be the same as the meaning "detect a potential" occurring on the surface of the body according to the heartbeat of an object. An apparatus for measuring an electrocardiogram may transmit and receive data with a user terminal by using a communication module. The communication module may include various types of communication modules such as a wireless Internet module, a near field communication module, and a mobile communication module.

The wireless Internet module refers to a module that is connected to an external network to perform communication according to communication protocols such as wireless LAN (WLAN), Wi-Fi, wireless broadband (Wibro), world interoperability for microwave access (Wimax), and high speed downlink packet access (HSDPA).

The near field communication module refers to a module for performing communication with an external device located at a short distance, according to near field communication methods such as Bluetooth, radio frequency identification (RFID), infrared data association (IrDA), ultra wideband (UWB), and ZigBee.

The mobile communication module refers to a module that accesses a mobile communication network to perform communication according to various types of mobile communication standards such as $3^{rd}$ generation (3G), $3^{rd}$ generation partnership project (3GPP), and long term evolution (LTE).

However, the communication module is not limited thereto, and may also apply other types of communication modules capable of performing communication with the electrocardiogram measuring apparatus 100 and transmitting and receiving various types of signals and data, in addition to those described above.

The electrocardiogram measuring apparatus 100 may further include a band-type mounting part. The mounting part may be made of a flexible material that may be deformed to fit a curved surface of the surface of the body, for example, an elastic, i.e., flexible fabric. The mounting part may be provided as a patch-type or a wearable type. As long as the electrocardiogram measuring apparatus 100 is worn through the mounting part, the electrocardiogram measuring apparatus 100 may detect a potential generated on the surface of the body by contacting the surface of the body of the object obj.

Figure 1B:
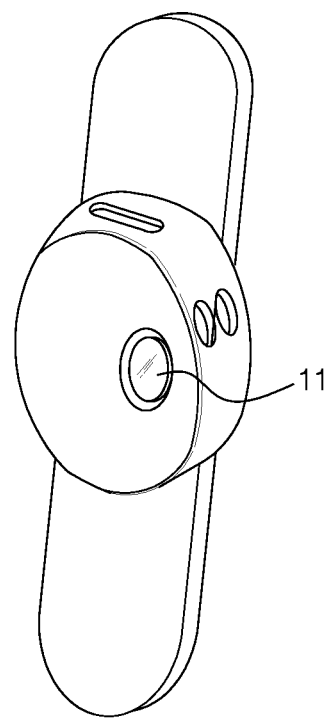
FIG. 1B is a perspective view of an apparatus for measuring an electrocardiogram.

As illustrated in FIG. 1B, the electrocardiogram measuring apparatus 100 may include an input unit 11. The electrocardiogram measuring apparatus 100 may receive a preset input through the input unit 11. The electrocardiogram measuring apparatus 100 has an outer appearance covered with cases 21 and 22. The cases 21 and 22 may form the outer appearance of the electrocardiogram measuring apparatus 100 and may accommodate and protect various elements in a space formed therein.

The cases 21 and 22 may be made of a plastic material that does not transfer heat or a metal material that is coated with a heat barrier material on the surface thereof. The cases 21 and 22 may be manufactured by, for example, an injection molding method, a 3D printing method, or a method of assembling small parts manufactured by injection molding.

Figure 1C:
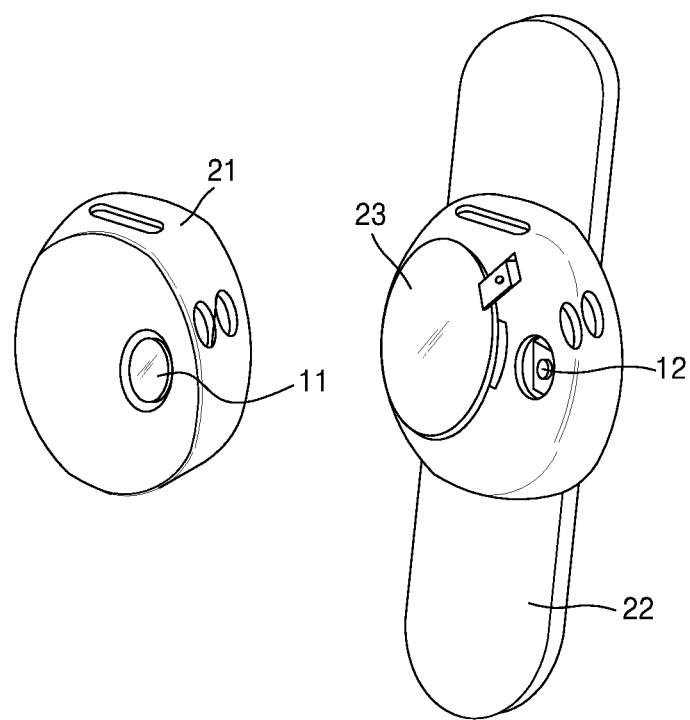
FIG. 1C is a side view of the apparatus for measuring an electrocardiogram of FIG. 1B.

In the electrocardiogram measuring apparatus 100 according to the embodiment illustrated in FIGS. 1B and 1C, the cases 21 and 22 are not vital elements and may not be installed as needed.

The input unit 11 may be arranged on the top of the case 21 and receive an input from a user. The input unit 11 may receive an on/off input, a touch input, an auditory data input, or the like. The input unit 11 may detect the sensitivity of the touch input. The input unit 11 may receive the on/off input and the auditory data input together. The input unit 11 may be implemented to enable the input of auditory data while the on/off input is generated. An input type of the input unit 11 may be the on/off input, the touch input, or the auditory data input, but is not limited thereto, and may be various types. The input unit 11 may receive a plurality of types of inputs.

As shown in FIG. 1C, when the case 21 of the electrocardiogram measuring apparatus 100 is removed, a battery 23 for supplying power and a button 12 are exposed. When the case 21 is removed, elements corresponding to a signal detector 110, a signal converter 120, a processor 130, an input unit 140, a power supply unit 150, a memory 160, a sensor unit 170, a communicator 180, and the like for operation of the electrocardiogram measuring apparatus 100 may be exposed.

Figure 2:
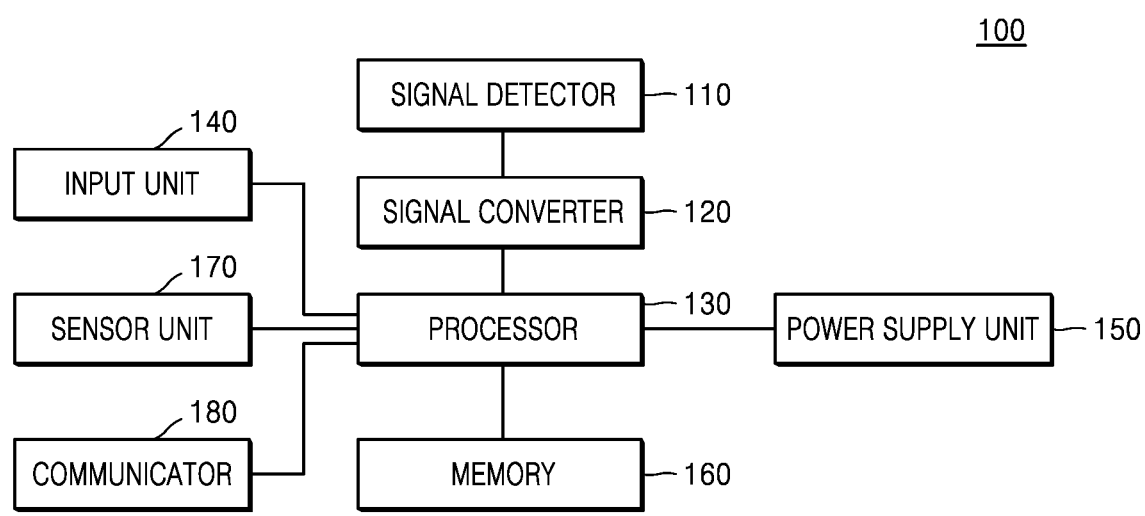
FIG. 2 is a block diagram of an apparatus for measuring an electrocardiogram, according to one or more embodiments.

FIG. 2 is a block diagram of an apparatus 100 for measuring an electrocardiogram according, to one or more embodiments.

As shown in FIG. 2, the apparatus 100 for measuring an electrocardiogram may include the signal detector 110, the signal converter 120, the processor 130, the input unit 140, the power supply unit 150, the memory 160, the sensor unit 170, and the communicator 180 to detect an electrical signal generated from the heart of an object. Note that a signal processing unit is not drawn in FIG. 2 because the signal processing unit is usually implemented in firmware of the processor 130. Here, the signal processing unit is implemented in hardware. But it is natural that the signal processing unit can be realized in firmware of the processor 130.

The signal detector 110 outputs an electrocardiogram analog signal by detecting an electrical signal from the heart of the object.

The signal converter 120 may convert the electrocardiogram analog signal into an electrocardiogram digital signal.

The processor 130 receives the electrocardiogram digital signal and stores the electrocardiogram digital signal in the memory 160. The processor 130 may transmit, to an external terminal, the electrocardiogram digital signal stored in the memory 160.

The processor 130 may receive a user input and/or generation time information of the user input and store the user input and/or the generation time information of the user input in the memory 160. The processor 130 may store, in the memory 160, an electrocardiogram digital signal merged with the user input. The processor 130 may receive the user input from the input unit 140 that is electrically connected or a user terminal that is connected through a communication network. The processor 130 may convert an electrocardiogram signal by using the received user input and generation time information of the user input. When an insertion input is received through the input unit 140 that is electrically connected, the processor 130 may receive a user input from the user terminal that is connected through the communication network. When the insertion input is received, the user terminal connected to the electrocardiogram measuring apparatus 100 may be changed to a user interface for receiving a user input.

The processor 130 may merge the electrocardiogram digital signal with the user input by using the generation time information of the user input and store, in the memory 160, the electrocardiogram digital signal merged with the user input. The processor 130 may transmit, to the external terminal, the electrocardiogram digital signal merged with the user input.

The processor 130 determines an insertion location of the user input in the electrocardiogram digital signal by using the generation time information of the user input and stores, in the memory 160, the electrocardiogram digital signal synchronized with the user input at the insertion location.

The processor 130 may divide the electrocardiogram digital signal into unit electrocardiogram signals in unit intervals and insert tags corresponding to a user input into the unit electrocardiogram signals in each unit interval. User inputs received in a first unit interval may be inserted into the first unit interval.

The processor 130 may transmit, to the external terminal, a part of the electrocardiogram digital signal determined on the basis of the generation time information of the user input. The processor 130 may merge the electrocardiogram digital signal with the user input, store, in the memory 160, the electrocardiogram digital signal merged with the user input and transmit, to the external terminal, a part of the electrocardiogram digital signal determined by the user input.

The processor 130 may stop transmitting the electrocardiogram digital signal to the external terminal considering a communication state with the external terminal. For example, the processor 130 may stop transmitting the electrocardiogram digital signal to the external terminal when the communication state with the external terminal is abnormal and restart transmitting the electrocardiogram digital signal to the external terminal when the communication state is normal again. The processor 130 may transmit the electrocardiogram digital signal while the communication state is abnormal.

The processor 130 may additionally generate a tag corresponding to a sensing value such as an apparatus temperature value detected through the sensor unit 170 and store, in the memory 160, the tag corresponding to the sensing value in association with the electrocardiogram digital signal. As used herein, the sensor unit 170 may be a movement sensor, an acoustic sensor, and a user input sensor, a temperature sensor, a motion sensor, a proximity sensor, a sound sensor, or the like.

The processor 130 may store, in the memory 160, information acquired by analyzing the electrocardiogram digital signal and a corresponding tag in association with the electrocardiogram digital signal. The information acquired by analyzing the electrocardiogram digital signal may be a heart rate, component information, the maximum magnitude value, time information of an inflection point, magnitude information of the inflection point, or the like. The maximum magnitude value refers to the maximum value of the magnitude from among the signal magnitudes of the electrocardiogram digital signal. The inflection point refers to a point at which a slope of a differential value of the electrocardiogram digital signal changes from positive to negative or negative to positive. The processor 130 may store, in the memory 160, a tag including at least one of the heart rate, the maximum magnitude value, the time information of the inflection point, and the magnitude information of the inflection point acquired by analyzing the electrocardiogram digital signal, in association with the electrocardiogram digital signal.

The processor 130 may acquire the exercise amount of an object, further generate a tag corresponding to the exercise amount, and store, in the memory 160, the tag corresponding to the momentum in association with the electrocardiogram digital signal.

When the processor 130 communicates with an external user terminal, the processor 130 may transmit, to the external user terminal, an electrocardiogram digital signal merged with a user input or a tag, in real time. Alternatively, when the measurement of the electrocardiogram digital signal is completed, the processor 130 may transmit, to the external user terminal, the electrocardiogram digital signal stored in the memory 160. When the measurement of the electrocardiogram digital signal is completed, the processor 130 may generate a measurement completion signal and start uploading, to the external terminal, the electrocardiogram digital signal stored in the memory 160 by the measurement completion signal. The measurement completion signal may be generated by an input from the external user terminal, an input from the input unit 140, or a preset measurement time, or may be generated after a preset measurement time from a measurement start time.

The processor 130 may be implemented to divide the electrocardiogram digital signal associated with the user input into preset time intervals and transmit, to the external user terminal, an electrocardiogram digital signal in a previous time interval prior to a current time interval.

The input unit 140 may receive at least one type of user input from among a touch input, an on/off button input, an auditory data input and a motion input. The input unit 140 may receive differently extracted information according to the type of input. For example, when the touch input is received, the input unit 140 may receive whether or not a touch is input, the sensitivity of the touch, and the like. When the on/off input is received, the input unit 140 may receive whether on or off is input, the number of on-offs per hour, and the like. When the auditory data input is received, the input unit 140 may receive input auditory data, input time information of the auditory data, and the like.

The power supply unit 150 supplies power to the signal detector 110, the signal converter 120, the processor 130, the input unit 140, the memory 160, the sensor unit 170, the communicator 180, and the like. The power supply unit 150 may use a rechargeable battery or a disposable battery.

The memory 160 may store data related to measurement of an electrocardiogram. The memory 160 may store information about the object, a measurement time, and data related to a measured electrocardiogram. The memory 160 may be hardware storing various types of pieces of data processed in the electrocardiogram measuring apparatus 100 and may store pieces of data processed by the processor 130 and pieces of data to be processed by the processor 130. The memory 160 may store a generated input, and a tag related to the input. The memory 160 may store an electrocardiogram digital signal and an electrocardiogram digital signal synchronized with a tag. The memory 160 may be implemented as various types, such as random access memory (RAM) such as dynamic random access memory (DRAM) and static random access memory (SRAM), read-only memory (ROM), and electrically erasable programmable read-only memory (EEPROM).

The sensor unit 170 senses temperature or senses movement. The sensor unit 170 may sense movements in x, y, and z-axis directions, movement of rotation in a first direction, and movement of rotation in a second direction. The sensor unit 170 may sense the momentum of an apparatus, a temperature value of the apparatus, physical pressure applied to the apparatus, and the like. The sensor unit 170 may include an element for sensing temperature, an element for sensing motion, and the like.

The communicator 180 may receive a control signal from the external user terminal. The communicator 180 may transmit measured data to the external user terminal.

Figure 3:
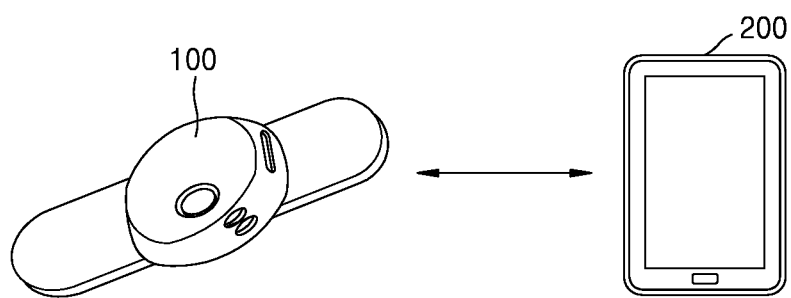
FIG. 3 is a view of a network environment connected to an apparatus for measuring an electrocardiogram.
Figure 4:
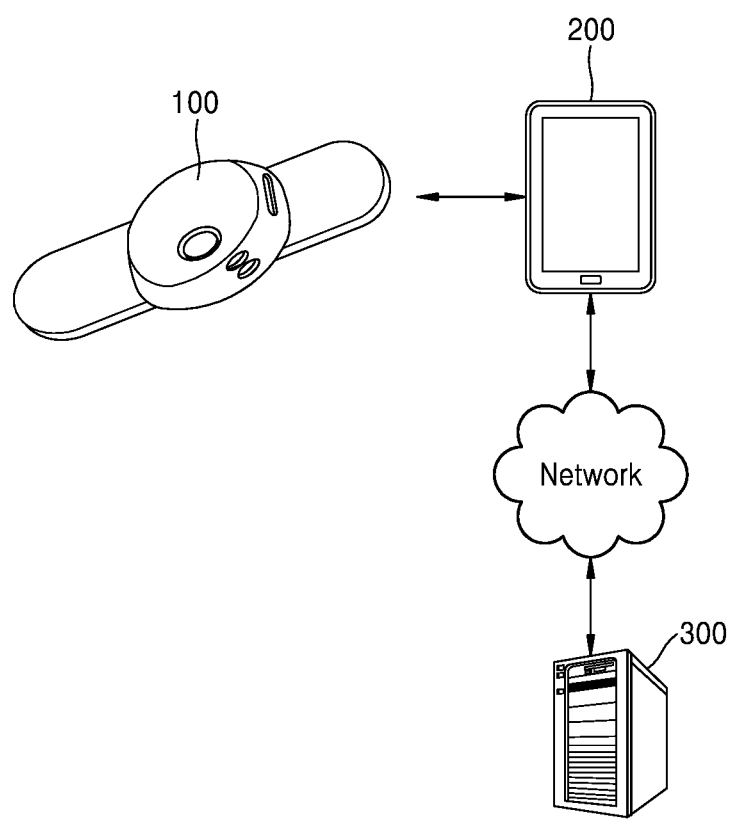
FIG. 4 illustrates another network environment connected to the apparatus for measuring an electrocardiogram.
Figure 5:
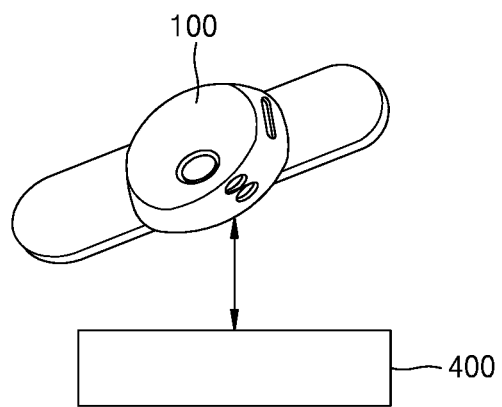
FIG. 5 illustrates further another network environment connected to the apparatus for measuring an electrocardiogram.

FIGS. 3 through 5 are views of a network environment connected to the electrocardiogram measuring apparatus 100.

As illustrated in FIG. 3, the electrocardiogram measuring apparatus 100 may operate while exchanging data with the user terminal 200. Here, the user terminal 200 may be used in a mobile phone, a smartphone, a laptop computer, or the like, but is not limited thereto. The user terminal 200 may be a mobile device, and the term "terminal" or "device" may be used interchangeably.

The electrocardiogram measuring apparatus 100 may transmit a measured electrocardiogram signal to the user terminal 200. The electrocardiogram measuring apparatus 100 may store an electrocardiogram signal including a tag related to an abnormal event related to the heart and transmit the electrocardiogram signal including the tag to the user terminal 200. The electrocardiogram measuring apparatus 100 may transmit, to the user terminal 200, measurement data generated by linking an electrocardiogram signal to a change in movement detected through a sensor unit, an input obtained through an input unit (a voice input unit, a text input unit, a button input unit, an image input unite, or the like), and input data received through the user terminal 200. The electrocardiogram measuring apparatus 100 may transmit, to the user terminal 200, an electrocardiogram signal including a tag related to a user input. The electrocardiogram measuring apparatus 100 may transmit, to the user terminal 200, an electrocardiogram signal synchronized with the user input. The electrocardiogram measuring apparatus 100 may transmit, to the user terminal 200, an electrocardiogram signal including a tag corresponding to an apparatus temperature value, a tag corresponding to electrocardiogram information such as heart rate, a tag corresponding to momentum information, and the like.

The user terminal 200 may store a received electrocardiogram signal, an electrocardiogram signal associated with a user input, a synchronized electrocardiogram signal, or an electrocardiogram signal including a tag related to the user input.

When user inputs are collected through the user terminal 200, the user terminal 200 may be implemented to input a user input related to an electrocardiogram signal in response to a user input posting signal from the electrocardiogram measuring apparatus 100 but is not limited thereto. The user terminal 200 may be implemented to input a user input related to an electrocardiogram signal without any signal from the electrocardiogram measuring apparatus 100.

The electrocardiogram measuring apparatus 100 may transmit, to the user terminal 200, measurement data in intervals in which an abnormal event occurs. The electrocardiogram measuring apparatus 100 may collect generation information of an abnormal event and transmit the collected generation information to the user terminal 200.

The electrocardiogram measuring apparatus 100 may transmit a measured electrocardiogram according to a request from the user terminal 200. The electrocardiogram measuring apparatus 100 may transmit a measured electrocardiogram according to a preset period.

The electrocardiogram measuring apparatus 100 may be controlled according to a control signal from the user terminal 200. The electrocardiogram measuring apparatus 100 may start or end measuring an electrocardiogram signal according to a measurement start signal or a measurement end signal from the user terminal 200. The electrocardiogram measuring apparatus 100 may delete data stored in a memory according to a data deletion signal from the user terminal 200.

The electrocardiogram measuring apparatus 100 may receive a control signal for a detection user input from the user terminal 200. When a user input corresponding to the detection user input is received, the electrocardiogram measuring apparatus 100 may transmit data regarding the detection user input to the user terminal 200. When a threshold heart rate is received as the detection user input, the electrocardiogram measuring apparatus 100 may transmit, to the user terminal 200, data regarding an electrocardiogram signal including a heart rate higher than or equal to the threshold heart rate.

The electrocardiogram measuring apparatus 100 may transmit information related to power to the user terminal 200. The electrocardiogram measuring apparatus 100 may transmit an alarm for the capacity of a power supply unit, whether or not the power supply unit is replaced, whether or not remaining power in the power supply unit is enough, and the like to be output through the user terminal 200. An alarm for notifying whether or not the electrocardiogram measuring apparatus 100 operates for a preset time may be also generated and transmitted to the user terminal 200. A time at which measurement is determined may be set through the user terminal 200 or may be set through an input unit in the electrocardiogram measuring apparatus 100, for example, may be set such as 24 hours, 48 hours, or the like.

The electrocardiogram measuring apparatus 100 may transmit information related to sensed movement to the user terminal 200. When the sensed movement is out of an excessive range or an electrocardiogram is not recorded, the electrocardiogram measuring apparatus 100 may transmit an alarm for this to the user terminal 200.

For convenience of description, the input unit 140 has been described as being included only in the electrocardiogram measuring apparatus 100, but an input device included in the user terminal 200 may also be used. For example, when auditory data or text data, a touch input, a movement touch, or the like are input through the user terminal 200, the electrocardiogram measuring apparatus 100 may merge a measured electrocardiogram digital signal with a user input by using time information of the user input and time-stamp recorded in the electrocardiogram measuring apparatus 100.

The user terminal 200 that communicates with the electrocardiogram measuring apparatus 100 may be registered through a preset registration process, and a single user terminal 200 or a plurality of user terminals 200 may be provided. As illustrated in FIG. 4, the electrocardiogram measuring apparatus 100 may operate while exchanging data with the user terminal 200 and an electrocardiogram management server 300.

The electrocardiogram management server 300 may manage electrocardiogram measurement data received from a plurality of electrocardiogram measuring apparatuses 100 and may use data of the electrocardiogram measuring apparatuses 100. The electrocardiogram measurement data may include an electrocardiogram signal itself and processed electrocardiogram data by measuring apparatus 100. Also, the electrocardiogram measurement data may include only electrocardiogram data of an interval in which an abnormal event occurs. The electrocardiogram management server 300 use data from the electrocardiogram measuring apparatus 100, which and may include information about a time when an electrocardiogram is measured, accumulated time information, information about a time when the electrocardiogram is not measured, information about a time when an abnormal event occurs, and the like.

The electrocardiogram management server 300 may manage electrocardiogram data from the electrocardiogram measuring apparatus 100 in association with an object. The electrocardiogram management server 300 may store electrocardiogram data for a first object in association with the first object. The electrocardiogram management server 300 may be designed to provide data of the first object (an electrocardiogram signal, a user input, an abnormal event, power-related information, and the like) to a user having authority over the first object. The user having authority over the first object may be at least one of a medical worker, a legal officer, and a person employed for management. The electrocardiogram management server 300 may transmit electrocardiogram data of an object requested by a request of the medical worker.

The electrocardiogram management server 300 may further receive context data from the electrocardiogram measuring apparatus 100. The electrocardiogram management server 300 may generate an analysis report by analyzing data received from the electrocardiogram measuring apparatus 100. The analysis report may include an event acquired through an electrocardiogram. The event may include an event related to movement of the heart, an event recorded by a user, an event recorded in a voice recognition method, movement and exercise amount of the user, a temperature value of a device, the heart rate, and the like. The analysis report may include data about an abnormal symptom of the heart. The analysis report may store, as separate data, a time point at which an abnormal symptom felt in the heart occurs, an electrocardiogram at the time point of the occurrence, and the like by using a tag related to an abnormal event and the like.

The electrocardiogram management server 300 may receive measurement data of the electrocardiogram measuring apparatus 100 through the user terminal 200.

As illustrated in FIG. 5, the electrocardiogram measuring apparatus 100 may be supplied with power through an external charging device 400. The external charging device 400 may charge the electrocardiogram measuring apparatus 100 by flowing a current through electromagnetic induction. The external charging device 400 may be configured in a pad shape, a cradle shape, an access point (AP) shape, a small base station shape, a stand shape, a ceiling-buried shape, a wall-hanging shape, or the like. One external charging device 400 may transmit power to a plurality of electrocardiogram measuring apparatuses 100 in a wireless or wired manner. The external charging device 400 may be implemented to check a power state of the electrocardiogram measuring apparatus 100 to automatically stop charging when the capacity of power is charged.

State information indicating whether or not the electrocardiogram measuring apparatus 100 is charged may be output through the electrocardiogram measuring apparatus 100 or the user terminal 200. When the electrocardiogram measuring apparatus 100 is completely charged, a notification or alert may be generated through the electrocardiogram measuring apparatus 100 or the user terminal 200.

The electrocardiogram measuring apparatus 100 may be implemented to have different power consumption for each power level. When a power level of the power supply unit is less than or equal to a preset first minimum value, the electrocardiogram measuring apparatus 100 may use power only to measure and store an electrocardiogram and may not use power to transmit data or the like to another device. When the power level of the power supply unit is less than or equal to a preset second minimum value, the electrocardiogram measuring apparatus 100 may adjust a period for measuring and storing an electrocardiogram longer.

Figure 6:
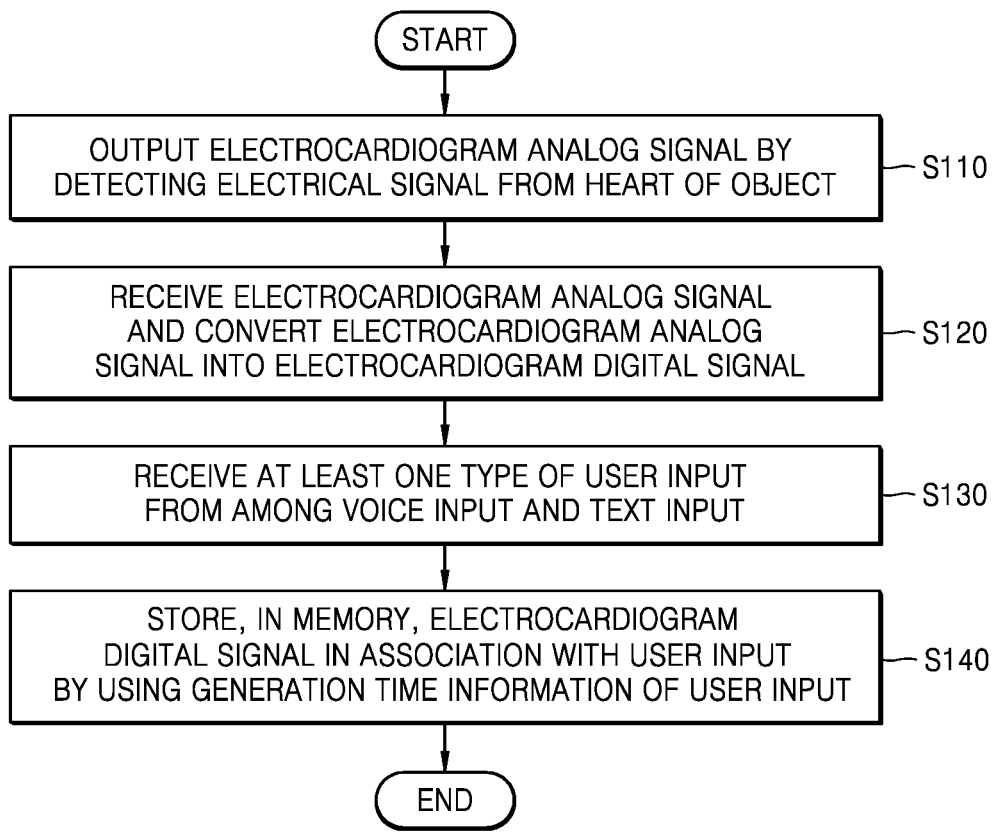
FIG. 6 is a flowchart of a method of generating an electrocardiogram signal associated with a user input, according to one embodiment.

FIG. 6 is a flowchart of a method of measuring an electrocardiogram, according to one or more embodiments.

As illustrated in FIG. 6, in operation S110, the electrocardiogram measuring apparatus 100 may output an electrocardiogram analog signal by detecting an electrical signal from the heart of an object.

In operation S120, the electrocardiogram measuring apparatus 100 may convert the electrocardiogram analog signal into an electrocardiogram digital signal.

In operation S130, the electrocardiogram measuring apparatus 100 may receive at least one type of user input from among a voice input and a text input.

In operation S140, the electrocardiogram measuring apparatus 100 stores, in a memory, the electrocardiogram digital signal in association with the user input by using generation time information of the user input.

The electrocardiogram measuring apparatus 100 may transmit, to a user terminal, the electrocardiogram digital signal associated with the user input. The electrocardiogram measuring apparatus 100 may divide the electrocardiogram digital signal into packets and transmit the packets to the user terminal. The electrocardiogram measuring apparatus 100 may modify the electrocardiogram digital signal to insert the user input received from the user terminal and a message corresponding to the user input.

Figure 7:
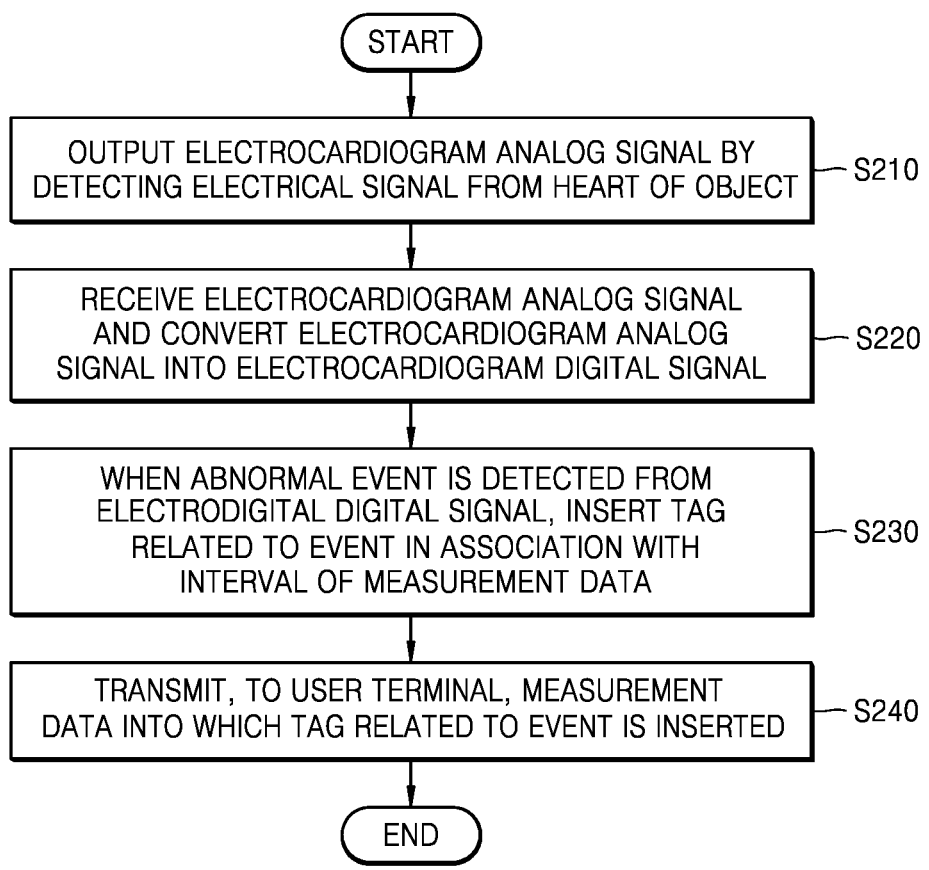
FIG. 7 is a flowchart of a method of generating an electrocardiogram signal associated with a user input, according to another embodiment.

FIG. 7 is a flowchart of a method of measuring an electrocardiogram, according to one or more embodiments.

As shown in FIG. 7, in operation S210, the electrocardiogram measuring apparatus 100 may output an electrocardiogram analog signal by detecting an electrical signal from the heart of an object.

In operation S220, the electrocardiogram measuring apparatus 100 may convert the electrocardiogram analog signal into an electrocardiogram digital signal.

In operation S230, when an abnormal event is detected from the electrocardiogram digital signal, the electrocardiogram measuring apparatus 100 detects a time point at which the abnormal event is detected and a corresponding interval of measurement data and inserts a tag related to an event in association with the interval of the measurement data.

The electrocardiogram measuring apparatus 100 generates the measurement data on the basis of the electrocardiogram digital signal and stores the measurement data in a memory. When an abnormal event is detected from the electrocardiogram digital signal, the electrocardiogram measuring apparatus 100 may detect a time point at which the abnormal event is detected and a corresponding interval of measurement data, insert a tag related to an event in association with the interval of the measurement data, and transmit, to an external user terminal, the measurement data into which the tag is inserted.

The tag related to the event may be generated by including information about pain related to the heart on the basis of context data detected at a time point at which the abnormal event is detected. The tag related to the event may be generated on the basis of data input through an input unit included in the electrocardiogram measuring apparatus 100. The tag related to the event may include input voice data, text data, image data, touch data, and the like. The tag related to the event may be set through an on/off button. The tag related to the event may be received through the user terminal.

In another embodiment, the tag related to the event may be generated by including information about pain related to the heart, life discomfort, and the like on the basis of context data detected at a time point at which the abnormal event is detected. The electrocardiogram measuring apparatus 100 may further collect context data in relation to the abnormal event. The electrocardiogram measuring apparatus 100 may sense context data through a sensor unit or may receive context data through a user terminal. Context data may include a change in movement adjacent to a detection time point of an abnormal event, an input value through an input unit adjacent to the event detection time point, input data input through a user terminal adjacent to the event detection time point, and the like.

In operation S240, the electrocardiogram measuring apparatus 100 transmits, to a user terminal, the measurement data into which the tag related to the event is inserted.

Therefore, the electrocardiogram measuring apparatus 100 may measure an electrocardiogram and simultaneously generate measurement data including an abnormal event occurring in heart activity and a tag related to an event.

Figure 8:
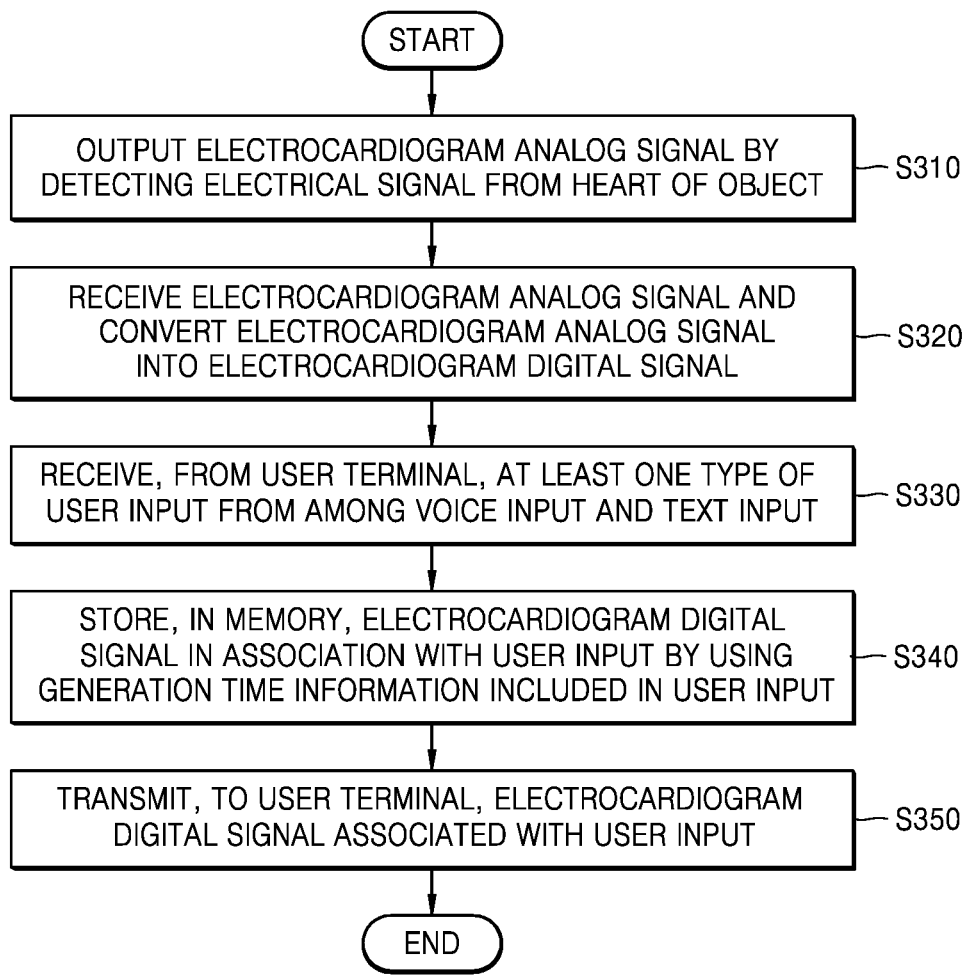
FIG. 8 is a flowchart of a method of generating an electrocardiogram signal associated with a user input, according to yet another embodiment.

As shown in FIG. 8, in operation S310, the electrocardiogram measuring apparatus 100 outputs an electrocardiogram analog signal by detecting an electrical signal from the heart of an object.

In operation S320, the electrocardiogram measuring apparatus 100 may receive the electrocardiogram analog signal and convert the electrocardiogram analog signal into an electrocardiogram digital signal.

In operation S330, the electrocardiogram measuring apparatus 100 receives, from the user terminal, at least one type of user input from among a voice input and a text input. The user terminal that transmits the user input may perform a registration procedure for transmitting the user input to the electrocardiogram measuring apparatus 100, in advance. The user terminal inputs a text input, a voice input, a touch input, or the like to be transmitted to the electrocardiogram measuring apparatus 100.

In another embodiment, the electrocardiogram measuring apparatus 100 may be implemented to receive an additional user input from the user terminal while an insertion input is generated through an input unit that is electrically connected.

In operation S340, the electrocardiogram measuring apparatus 100 determines an insertion location of the user input by using generation time information included in the user input, synchronizes the user input and the electrocardiogram digital signal by using the insertion location, and stores, in a memory, the electrocardiogram digital signal synchronized with the user input. In this case, the generation time information may be generated by the user terminal or may be generated as a time at which an insertion input in the electrocardiogram measuring apparatus 100 is generated.

In operation S350, the electrocardiogram measuring apparatus 100 may transmit, to the user terminal, the electrocardiogram digital signal associated with the user input.

In another embodiment, the electrocardiogram measuring apparatus 100 may transmit the electrocardiogram digital signal to the user terminal without operation S330. The user terminal that receives the electrocardiogram digital signal may modify the electrocardiogram digital signal to insert the user input generated from the user terminal.

As a result, the electrocardiogram measuring apparatus 100 may generate an electrocardiogram digital signal associated with a user input that is input through the user terminal.

Figure 9:
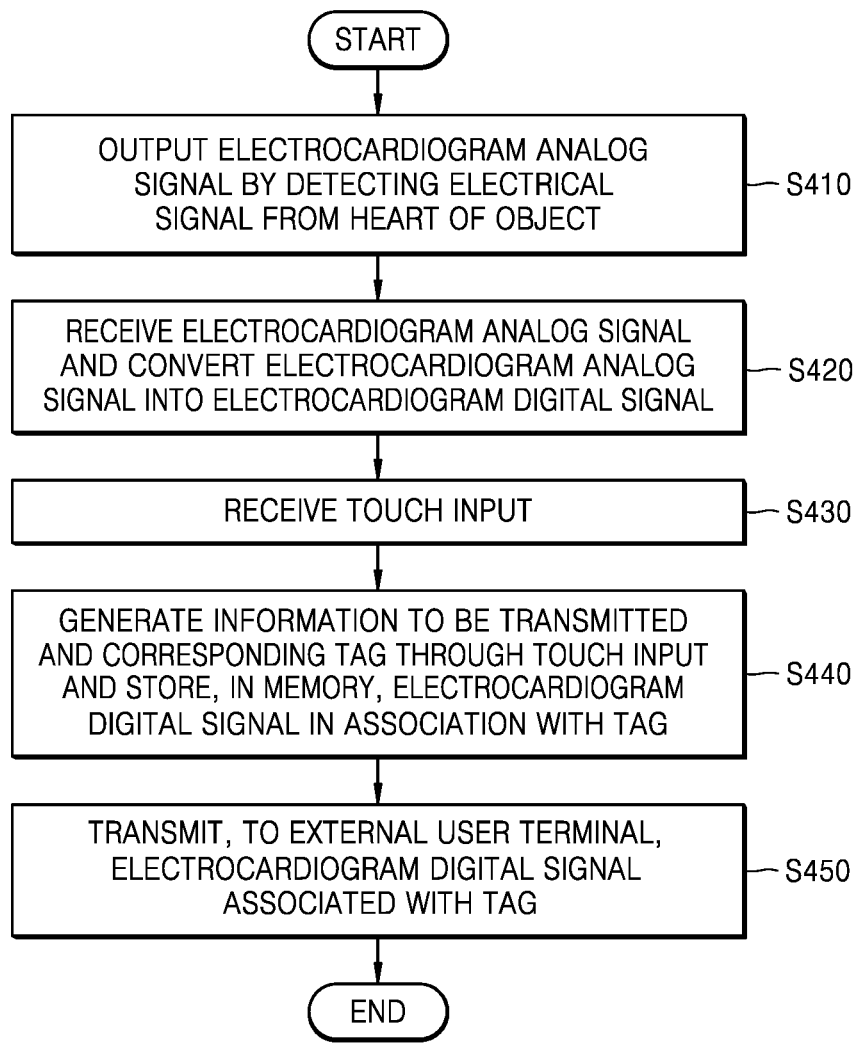
FIG. 9 is a flowchart of a method of generating an electrocardiogram signal associated with a user input, according to yet another embodiment.

As shown in FIG. 9, in operation S410, the electrocardiogram measuring apparatus 100 outputs an electrocardiogram analog signal by detecting an electrical signal from the heart of an object. In operation S420, the electrocardiogram measuring apparatus 100 receives the electrocardiogram analog signal and converts the electrocardiogram analog signal into an electrocardiogram digital signal.

In operation S430, the electrocardiogram measuring apparatus 100 receives a touch input. The touch input may be acquired from a user terminal or may be acquired through a provided input unit.

In operation S440, the electrocardiogram measuring apparatus 100 may generate information to be transmitted and a corresponding tag through the touch input and store, in a memory, the electrocardiogram digital signal in association with the tag. The electrocardiogram measuring apparatus 100 may generate the information to be transmitted and the corresponding tag through the touch input, considering an input time point, an input length, an input intensity, and the like of the touch input.

In operation S450, the electrocardiogram measuring apparatus 100 transmits, to the external user terminal, the electrocardiogram digital signal associated with the tag. Accordingly, the electrocardiogram measuring apparatus 100 may store a tag according to an input time point, an input length, an input intensity, and the like of a touch input, in synchronization with an electrocardiogram signal. According to an input length and an input intensity of a touch, information such as pain felt in the heart may be included.

Figure 10:
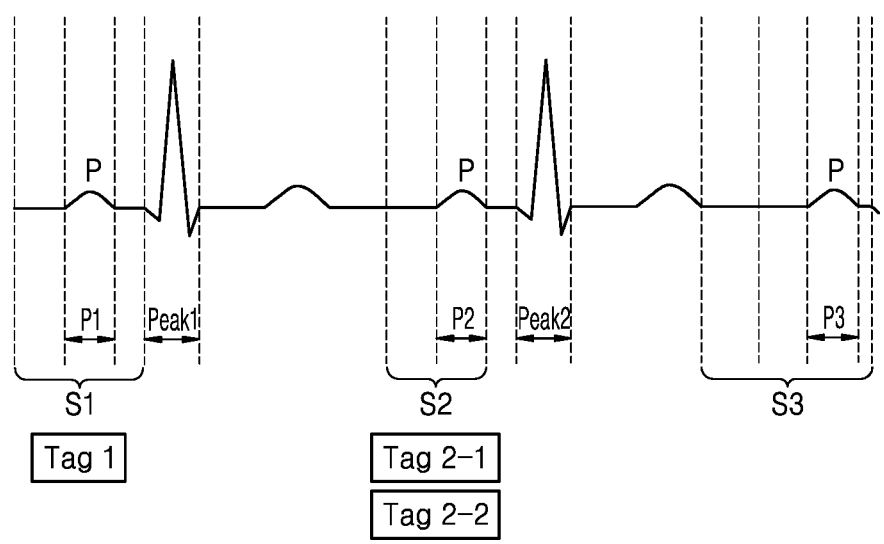
FIG. 10 is an example view of an electrocardiogram signal with tags tagged at each time interval.

As shown in FIG. 10, the electrocardiogram measuring apparatus 100 may generate an electrocardiogram signal with a tag tagged at each time interval.

The apparatus described above may be implemented with hardware components, software components, and/or combinations of hardware components and software components. For example, the apparatus and components described in one or more embodiments may be implemented, for example, by using one or more general-purpose computers or special-purpose computers such as a processor, a controller, an arithmetic logic unit (ALU), a digital signal processor, a microcomputer, a field programmable gate array (FPGA), a programmable logic unit (PLU), a microprocessor, or any other devices capable of executing and responding to instructions. A processing unit may perform an operating system (OS) and one or more software applications executed on the OS. Also, the processing unit may access, store, control, process, and generate data in response to execution of software. For convenience of understanding, while one processing unit has been described as being used, it will be understood by one of ordinary skill in the art that the processing unit may include a plurality of processing elements and/or a plurality of types of processing elements. For example, the processing unit may include a plurality of processors or one processor and one controller. Also, the processing unit may include another processing configuration such as a parallel processor.

Software may include a computer program, code, instructions, or a combination of one or more thereof and may configure the processing unit to operate as wanted or instruct the processing unit independently or collectively. Software and/or data may be permanently or temporarily embodied in any type of machine, component, physical device, virtual equipment, computer storage medium or device, or transmitted signal wave to be interpreted by the processing unit or to provide the processing unit with instructions or data. Software may be distributed over networked computer systems and may be stored or executed in a distributed manner. Software and/or data may be stored on one or more computer-readable recording media.

The method according to one or more embodiments may be implemented in the form of a computer instruction that may be executed through various types of computer units and recorded on a computer-readable recording medium. The computer-readable recording medium may include program instructions, data files, data structures, or the like alone or in combination. The program instructions recorded on the medium may be specially designed and configured for an embodiment or may be known and available to one of ordinary skill in computer software. Examples of the computer-readable recording medium include magnetic media such as hard disks, floppy disks, and magnetic tapes, optical media such as CD-ROM and DVD, magneto-optical media such as floptical disks, and hardware devices specially configured to store and perform program instructions such as ROM, RAM, and flash memory. Examples of the program instructions include high-level language code that may be executed by a computer using an interpreter or the like, as well as machine language code made by a compiler. The hardware device described above may be configured to operate as one or more software modules to perform operations of the embodiments, and the reverse is the same.

According to one or more embodiments, a user input related to heart movement may be received, and an electrocardiogram digital signal associated with a tag corresponding to the user input may be generated.

According to one or more embodiments, a user input that is input through an external user terminal may be received, and an electrocardiogram signal associated with a tag corresponding to the user input may be generated.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An apparatus for measuring an electrocardiogram and storing an electrocardiogram signal merged with a user input, the apparatus comprising:
    a signal detector outputting an electrocardiogram analog signal by detecting an electrical signal from a heart of an object;
    a signal converter receiving the electrocardiogram analog signal and converting the electrocardiogram analog signal into an electrocardiogram digital signal;
    a motion sensor sensing movements of the apparatus for measuring the electrocardiogram in x, y, and z-axis directions;
    an input unit receiving at least one type of the user input from among a voice input, a button input, and a touch input;
    a processor receiving the at least one type of user input, and storing the electrocardiogram digital signal in an internal memory;
    a communicator communicating with an external terminal to transmit the electrocardiogram digital signal to the external terminal; and
    a mounting part being made of a flexible material and is implemented to be attached to a body of the object such that the apparatus is worn through the mounting part as a patch type,
    wherein the processor additionally generates data related to the movements and at least one tag related to the user input, the processor further inserts the at least one tag into the electrocardiogram digital signal, and the processor transmits the electrocardiogram digital signal and the data related to the movements to the external terminal to generate an analysis report based on the electrocardiogram digital signal and the data related to the movements in an external device; and
    wherein the processor further collects context data in relation to an abnormal event related to the heart of the object via the motion sensor and the external terminal, the context data including a change in the movements adjacent to a detection time point of the abnormal event, generates a first tag including information on the basis of the context data, inserts the first tag into the electrocardiogram digital signal, and stores the electrocardiogram digital signal in the internal memory.

2. The apparatus of claim 1, wherein:
    the communicator, wirelessly or via wire, communicates with the external terminal, and
    the processor transmits, to the external terminal, a part of the electrocardiogram digital signal determined by the user input.

3. The apparatus of claim 2, wherein the processor stops transmitting the electrocardiogram digital signal to the external terminal when a disconnection of communication with the external terminal is detected and restarts transmitting the electrocardiogram digital signal to the external terminal when a state of the communication with the external terminal returns to be normal.

4. The apparatus of claim 3, wherein the processor additionally transmits, to the external terminal, an electrocardiogram digital signal stored while not communicating with the external terminal.

5. The apparatus of claim 1, wherein the processor uploads, to the external terminal, the electrocardiogram digital signal stored in the internal memory after a measurement completion signal is generated.

6. The apparatus of claim 5, wherein the measurement completion signal is generated by an input from the external terminal, the at least one type of the user input from the input unit, or a preset measurement time.

7. The apparatus of claim 1, wherein the user input additionally includes time information.

8. The apparatus of claim 1, wherein the at least one tag includes a heart rate, a maximum magnitude value, time information of an inflection point, magnitude information of an the inflection point, or a combination thereof.

9. A method of measuring an electrocardiogram and storing an electrocardiogram digital signal merged with a user input, the method comprising:

outputting, by a processing system including a processor, an electrocardiogram analog signal by detecting an electrical signal from a heart of an object, the outputting being performed by an apparatus for measuring an electrocardiogram;

receiving, by the processing system, the electrocardiogram analog signal and converting the electrocardiogram analog signal into an electrocardiogram digital signal, the receiving and converting being performed by the apparatus;

receiving, by the processing system, at least one type of user input from at least one among a voice input, a button input, and a touch input, the receiving being performed by the apparatus;

sensing, by the processing system, movements of the apparatus for measuring the electrocardiogram in x, y, and z-axis directions by a motion sensor;

receiving, by the processing system, the at least one type of user input, and storing the electrocardiogram digital signal in an internal memory by the apparatus;

generating, by the processing system, data related to the movements and at least one tag related to the user input;

inserting, by the processing system, the at least one tag into the electrocardiogram digital signal;

communicating, by the processing system, with an external terminal to transmit the electrocardiogram digital signal and the data related to the movements to the external terminal to generate an analysis report based on the electrocardiogram digital signal and the data related to the movement in an external device, the communicating being performed by the apparatus;

collecting, by the processing system, context data in relation to an abnormal event related to the heart of the object via the motion sensor and the external terminal, the context data including a change in movement adjacent to a detection time point of the abnormal event;

generating, by the processing system, a first tag including information on the basis of the context data;

inserting, by the processing system, the first tag into the electrocardiogram digital signal; and storing, by the processing system, the electrocardiogram digital signal in the internal memory.

10. The method of claim 9, wherein the communicating with the external terminal comprises transmitting, to the external terminal, a part of the electrocardiogram digital signal determined by the user input, as needed.

11. The method of claim 10, further comprising stopping, by the processing system, transmitting the electrocardiogram digital signal to the external terminal when a disconnection of communication with the external terminal is detected and restarting transmitting the electrocardiogram digital signal to the external terminal when a state of the communication with the external terminal is normal.

12. The method of claim 11, further comprising additionally transmitting, by the processing system, to the external terminal, an electrocardiogram digital signal stored while not communicating with the external terminal.

13. The method of claim 9, further comprising uploading by the processing system, to the external terminal, the electrocardiogram digital signal stored in the internal memory after a measurement completion signal is generated.

14. The method of claim 13, wherein the measurement completion signal is generated by an input from the external terminal, the at least one type of user input from a provided input unit, or a preset measurement time.

15. The method of claim 9, wherein the user input additionally includes time information.

16. The method of claim 9, wherein the at least one tag includes a heart rate, a maximum magnitude value, a time information of an inflection point, a magnitude information of an the inflection point, or a combination thereof.

* * * * *